(12) United States Patent
Wallace et al.

(10) Patent No.: US 6,312,435 B1
(45) Date of Patent: *Nov. 6, 2001

(54) SURGICAL INSTRUMENT WITH EXTENDED REACH FOR USE IN MINIMALLY INVASIVE SURGERY

(75) Inventors: Daniel T. Wallace, Redwood City; David J. Rosa, San Jose; Frederic H. Moll, Woodside, all of CA (US)

(73) Assignee: Intuitive Surgical, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/415,949

(22) Filed: Oct. 8, 1999

(51) Int. Cl.[7] .................................................. A61B 19/00
(52) U.S. Cl. ............................................................ 606/130
(58) Field of Search ................................ 606/130, 43, 52, 606/157, 170, 174, 206, 211; 600/429

(56) References Cited

U.S. PATENT DOCUMENTS

| | | | |
|---|---|---|---|
| 4,367,998 | * 1/1983 | Causer | 414/4 |
| 4,696,501 | 9/1987 | Webb . | |
| 4,744,363 | 5/1988 | Hasson . | |
| 4,750,475 | 6/1988 | Yoshihashi . | |
| 4,830,569 | * 5/1989 | Jannborg | 414/729 |
| 5,141,519 | 8/1992 | Smith et al. . | |
| 5,201,743 | 4/1993 | Haber et al. . | |
| 5,209,747 | 5/1993 | Knoepfler . | |
| 5,350,391 | * 9/1994 | Iacovelli | 606/170 |
| 5,374,277 | * 12/1994 | Hassler | 606/207 |
| 5,649,956 | * 7/1997 | Jensen et al. | 606/205 |
| 5,695,521 | * 12/1997 | Anderhub | 606/205 |
| 5,792,135 | * 8/1998 | Madhani et al. | 606/1 |
| 5,808,665 | * 9/1998 | Green | 348/65 |
| 5,817,084 | * 10/1998 | Jensen | 606/1 |
| 5,855,583 | * 1/1999 | Wand et al. | 606/139 |
| 5,876,325 | * 3/1999 | Mizuno et al. | 600/102 |

FOREIGN PATENT DOCUMENTS

9950721 * 10/1999 (WO) .................................. 606/130

OTHER PUBLICATIONS

"Task 2: Miniature end effector—A preliminary design" pp. 32–47.

* cited by examiner

*Primary Examiner*—Jeffrey A. Smith
*Assistant Examiner*—Eduardo C. Robert
(74) *Attorney, Agent, or Firm*—Townsend Townsend & Crew LLP; Mark D. Barrish, Esq.

(57) ABSTRACT

An improved surgical instrument, which can advantageously be used in the field of minimally invasive surgery, is provided. A method of performing a surgical procedure with such an improved surgical instrument is also provided. The improved surgical instrument includes an elongate shaft defining opposed ends. An end effector is mounted on one of the ends of the shaft. The end effector has at least one finger pivotally connected at the one end of the shaft selectively to be displaceable angularly about an end effector pivot axis at the one end of the shaft, such that a free end of the finger is displaceable about the end effector pivot axis. The finger has a length, defined between its free end and the end effector pivot axis, of at least 18 mm.

28 Claims, 10 Drawing Sheets

SURGICAL INSTRUMENT WITH EXTENDED REACH FOR USE IN MINIMALLY INVASIVE SURGERY

CROSS-REFERENCES TO RELATED APPLICATIONS

This application is related to the following patents and patent applications, the full disclosures of which are incorporated herein by reference: PCT International Application No. PCT/US98/19508, entitled "Robotic Apparatus", filed on Sep. 18, 1998, U.S. application Serial No. 60/111,713, entitled "Surgical Robotic Tools, Data Architecture, and Use", filed on Dec. 8, 1998; U.S. application Serial No. 60/111,711, entitled "Image Shifting for a Telerobotic System", filed on Dec. 8, 1998; U.S. application Ser. No. 09/378,173, entitled "A Stereo Imaging System and Method for Use in Telerobotic Systems", filed on Aug. 20, 1999; U.S. application Ser. No. 09/398,507, entitled "Master Having Redundant Degrees of Freedom", filed on Sep. 17, 1999, U.S. application Ser. No. 09/399,457, entitled "Dynamic Association of Master and Slave in a Minimally Invasive Telesurgery System", filed on Sep. 17, 1999; U.S. application Ser. No. 09/373,678, entitled "Camera Referenced Control in a Minimally Invasive Surgical Apparatus", filed on Aug. 13, 1999; U.S. application Ser. No. 09/398,958, entitled "Surgical Tools for Use in Minimally Invasive Telesurgical Applications", filed on Sep. 17, 1999; and U.S. Pat. No. 5,808,665, entitled "Endoscopic Surgical Instrument and Method for Use", issued on Sep. 15, 1998.

BACKGROUND OF THE INVENTION

This invention generally relates to a surgical instrument. In particular, the invention relates to a surgical instrument and a method of performing a surgical procedure. The surgical instrument can advantageously, although not necessarily exclusively, be used in robotically controlled minimally invasive surgical operations.

Minimally invasive medical techniques are aimed at reducing the amount of extraneous tissue which may be damaged during diagnostic or surgical procedures, thereby reducing patient recovery time, discomfort, and deleterious side effects. Many surgeries are performed each year in the United States. A significant amount of these surgeries can potentially be performed in a minimally invasive manner. However, only a relatively small percentage of surgeries currently use minimally invasive techniques due to limitations of minimally invasive surgical instruments and techniques currently used, and the difficulty experienced in performing surgeries using such traditional instruments and techniques.

Advances in minimally invasive surgical technology could dramatically increase the number of surgeries performed in a minimally invasive manner. The average length of a hospital stay for a standard surgery is significantly longer than the average length for the equivalent surgery performed in a minimally invasive surgical manner. Thus, expansion in the use of minimally invasive techniques could save millions of hospital days, and consequently millions of dollars annually, in hospital residency costs alone. Patient recovery times, patient discomfort, surgical side effects, and time away from work can also be reduced by expanding the use of minimally invasive surgery.

Traditional forms of minimally invasive surgery include endoscopy. One of the more common forms of endoscopy is laparoscopy, which is minimally invasive inspection or surgery within the abdominal cavity. In traditional laparoscopic surgery a patient's abdominal cavity is insufflated with gas and cannula sleeves are passed through small incisions in the musculature of the patient's abdomen to provide entry ports through which laparoscopic surgical instruments can be passed in a sealed fashion. Such incisions are typically about ½ inch (about 12 mm) in length.

The laparoscopic surgical instruments generally include a laparoscope for viewing the surgical field and working tools defining end effectors. Typical surgical end effectors include clamps, graspers, scissors, staplers, and needle holders, for example. The working tools are similar to those used in conventional (open) surgery, except that the working end or end effector of each tool is separated from its handle by a long extension tube, typically of about 12 inches (about 300 mm) in length, for example, so as to permit the surgeon to introduce the end effector to the surgical site and to control movement of the end effector relative to the surgical site from outside a patient's body.

To perform surgical procedures, the surgeon typically passes these working tools or instruments through the cannula sleeves to the internal surgical site and manipulates the instruments or tools from outside the abdomen by sliding them in and out through the cannula sleeves, rotating them in the cannula sleeves, levering (i.e., pivoting) the instruments against the abdominal wall and actuating the end effectors on distal ends of the instruments from outside the abdominal cavity. The instruments normally pivot around centers defined by the incisions which extend through the muscles of the abdominal wall. The surgeon typically monitors the procedure by means of a television monitor which displays an image of the surgical site captured by the laparoscopic camera. Typically, the laparoscopic camera is also introduced through the abdominal wall so as to capture the image of the surgical site. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

There are many disadvantages relating to such traditional minimally invasive surgical (MIS) techniques. For example, existing MIS instruments deny the surgeon the flexibility of tool placement found in open surgery. Difficulty is experienced in approaching the surgical site with the instruments through the small incisions. The length and construction of many endoscopic instruments reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the expansion of the use of minimally invasive surgery.

Minimally invasive telesurgical systems for use in surgery have been and are still being developed to increase a surgeon's dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

Typically, such a telesurgery system can be provided with at least two master control devices (one for each of the surgeon's hands), which are normally operatively associated with two robotic arms on each of which a surgical instrument is mounted. Operative communication between master control devices and associated robotic arm and instrument assemblies is typically achieved through a control system. The control system typically includes at least one processor which relays input commands from the master control devices to the associated robotic arm and instrument assemblies and from the arm and instrument assemblies to the associated master control devices in the case of, e.g., force feedback, or the like.

One object of the present invention is to provide an improved surgical instrument for use in a telesurgery system as described above.

SUMMARY OF THE INVENTION

In accordance with one aspect of the invention, there is provided a surgical instrument. The surgical instrument comprises an elongate shaft defining opposed ends. It further comprises an end effector, for performing a surgical operation, mounted at one of the ends of the shaft. The end effector may have two fingers pivotally connected relative to each other to be angularly displaceable relative to each other about an end effector pivot axis at the one end of the shaft. Each finger defines a free end remote from the end effector pivot axis and is of a length defined between its free end and the end effector pivot axis of at least ¾ inch (about 18 mm).

Typically, the length falls in the range between about 18 mm and 30 mm.

The surgical instrument may further comprise at least one elongate actuation element extending along the shaft. The actuation element may be operatively connected to the end effector at the one end of the shaft so as to enable the fingers of the end effector selectively to be displaced angularly relative to each other about the end effector pivot axis by selective actuation of the elongate actuation element.

The surgical instrument may further comprise at least one transmission member mounted on the other end of the shaft. The transmission member may be operatively connected to the elongate actuation element so as to cause actuation of the elongate actuation element in response to actuation of the transmission member.

The elongate shaft may define an internal longitudinally extending passage. The elongate actuation element may be positioned inside the passage to extend internally along the shaft.

In accordance with another aspect of the invention, there is provided a method of performing a surgical procedure. The method comprises passing a surgical instrument having an elongate shaft, at one end of which an end effector is pivotally mounted, through an entry port in a patient body into a position in which the end effector is positioned within the patient body and an opposed end of the shaft is positioned outside the patient body. The end effector may have two fingers pivotally connected to each other to be displaceable angularly relative to each other about an end effector pivot axis. Each finger defines a free end remote from the end effector pivot axis and is of a length defined between its free end and the end effector pivot axis of at least ¾ inch (about 18 mm). The method comprises connecting the surgical instrument in a robotically controlled system and actuating the end effector from outside the patient body by means of the robotically controlled system so as to cause the fingers selectively to move toward and away from each other thereby to perform at least part of the surgical procedure.

The surgical instrument may comprise at least one elongate actuation element extending along the shaft. The actuation element may be operatively connected to the end effector at the one end of the shaft so as to enable the fingers of the end effector selectively to be displaced angularly relative to each other about the end effector pivot axis by selective actuation of the elongate actuation element at the opposed end of the shaft. Actuating the end effector from outside the patient body by means of the robotically controlled system may then include causing the robotically controlled system to actuate the elongate actuation element.

Connecting the surgical instrument in a robotically controlled system may include releasably mounting the surgical instrument on a robotically controlled arm.

DESCRIPTION OF THE PREFERRED EMBODIMENTS

Figure 1:
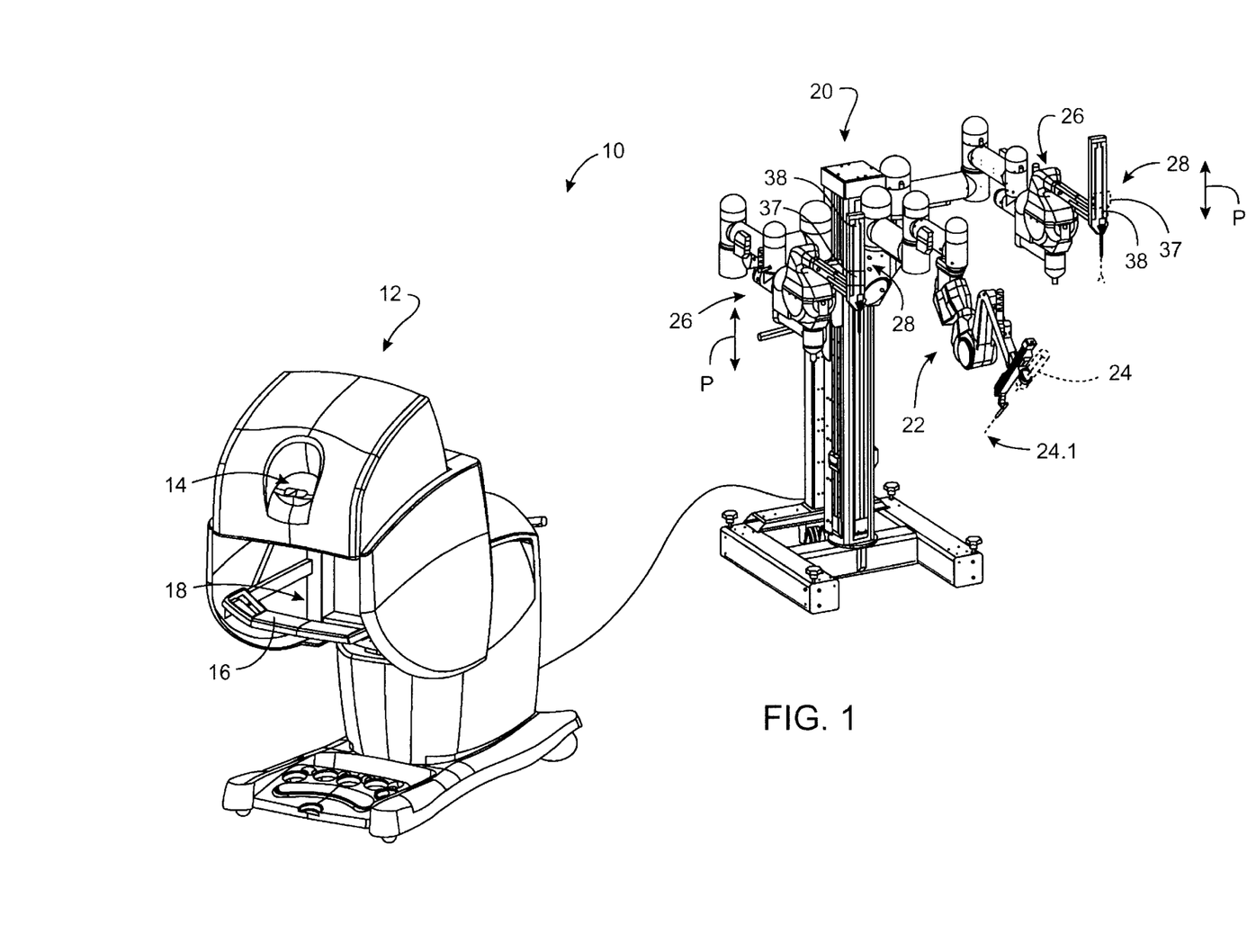
FIG. 1 shows a three-dimensional view of an operator control station, or surgeon's console, and a surgical work station, or cart, of a telesurgical system, the cart carrying three robotically controlled arms, the movement of the arms being remotely controllable from the control station.

Referring to FIG. 1 of the drawings, a minimally invasive telesurgical system, or robotically controlled surgical system, is generally indicated by reference numeral 10. The system 10 includes a control station, or surgeon's console, generally indicated by reference numeral 12. The station 12 includes an image display or viewer 14 where an image of a surgical site is displayed in use. A support 16 is provided on which an operator, typically a surgeon, can rest his or her forearms while gripping two master control devices, one in each hand. The master control devices are positioned in a space 18 inwardly beyond the support 16. When using the control station 12, the surgeon typically sits in a chair in front of the control station 12, positions his or her eyes in front of the viewer 14 and grips the master controls one in each hand while resting his or her forearms on the support 16.

The system 10 further includes a surgical work station, or cart, generally indicated by reference numeral 20. In use, the cart 20 is positioned in close proximity to a patient requiring surgery and is then normally caused to remain stationary until a surgical procedure to be performed by means of the system 10 has been completed. The cart 20 typically has wheels or castors to render it mobile. The station 12 is typically positioned remote from the cart 20 and can be separated from the cart 20 by a great distance, even miles away, but will typically be used within an operating room with the cart 20.

The cart 20 typically carries at least three robotic arm assemblies. One of the robotic arm assemblies, indicated by reference numeral 22, is arranged to hold an image capture device 24, e.g., an endoscope, or the like. Each of the other two arm assemblies 26, 26 respectively, is arranged to hold a robotically controlled surgical instrument 28. The endoscope 24 has an object viewing end 24.1 at a remote end of an elongate shaft thereof. It will be appreciated that the endoscope 24 has an elongate shaft to permit its viewing end 24.1 to be inserted through an entry port in a patient's body so as to access an internal surgical site. The endoscope 24 is operatively connected to the viewer 14 to display an image captured at its viewing end 24.1 on a display area of the viewer 14. Each robotic arm assembly 26, 26 is normally operatively connected to one of the master controls. Thus, the movement of the robotic arm assemblies 26, 26 is controlled by manipulation of the master controls. The instruments 28 on the robotic arm assemblies 26, 26 have end effectors which are mounted on wrist-like mechanisms which are pivotally mounted on distal ends of elongate shafts of the instruments 28. It will be appreciated that the instruments 28 have elongate shafts to permit the end effectors to be inserted through entry ports in a patient's body so as to access the internal surgical site. Movement of the end effectors relative to the ends of the shafts of the instruments 28 is also controlled by the master controls. When a surgical procedure is to be performed, the cart 20 carrying the robotic arms 22, 26, 26 is wheeled to the patient and is normally maintained in a stationary position relative to, and in close proximity to, the patient, during the surgical procedure.

Figure 2:
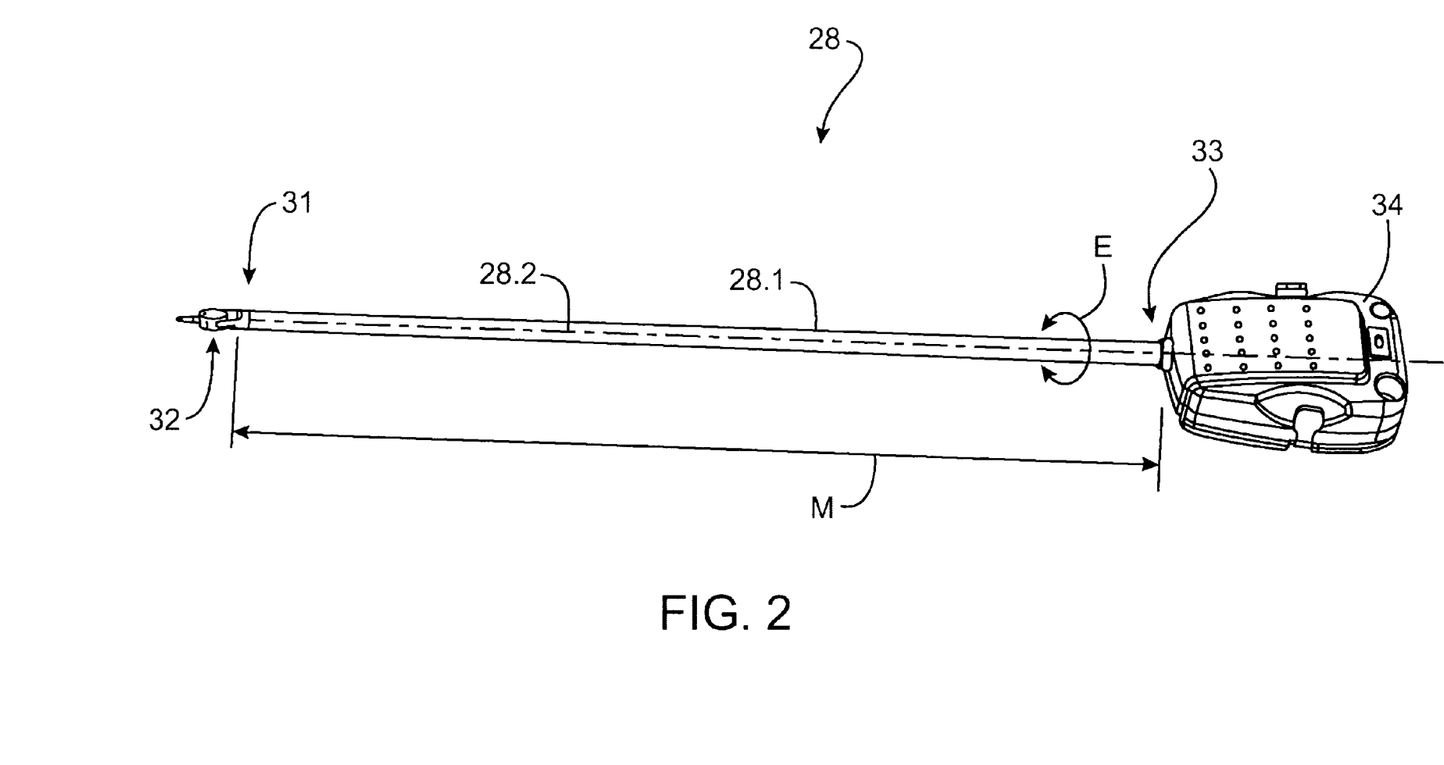
FIG. 2 shows, at an enlarged scale, a three-dimensional view of a typical surgical instrument used with the system shown in FIG. 1.

Referring to FIG. 2 of the drawings, the surgical instrument 28 will now be described in greater detail. The surgical instrument 28 includes an elongate shaft 28.1. The elongate shaft 28.1 defines opposed ends 31 and 33. The wrist-like mechanism, generally indicated by reference numeral 32, is located at the end 31 of the shaft 28.1. A housing 34, arranged releasably to couple the instrument 28 to one of the robotic arm assemblies 26, 26 is located at the other end 33 of the shaft 28.1. Referring again to FIG. 1 of the drawings, the instrument 28 is typically releasably mountable on a carriage 37 which can be driven to translate along a linear guide formation 38 of the arm 26 in the direction of arrows P.

Figure 4:
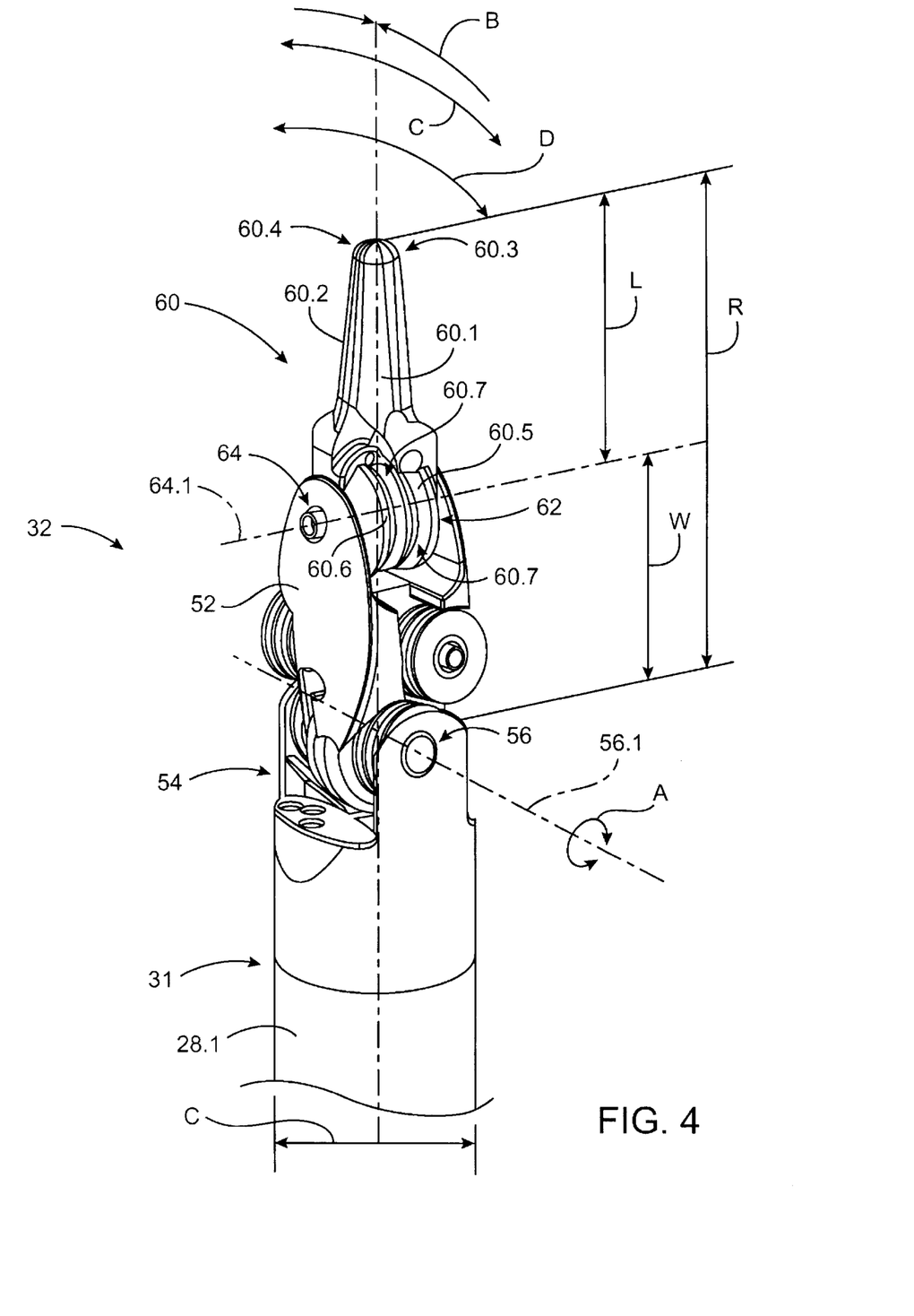
FIG. 4 shows a three-dimensional view of an end effector of the surgical instrument shown in FIGS. 2 and 3.

Referring now to FIG. 4 of the drawings, the wrist-like mechanism 32 will now be described in greater detail. The wrist-like mechanism 32 includes a wrist member 52. One end portion of the wrist member 52 is pivotally mounted in a clevis, generally indicated at 54, on the end 31 of the shaft 28.1 by means of a wrist pivot 56. The wrist member 52 can pivot in the direction of arrows A about a wrist pivot axis 56.1 defined by the wrist pivot 56. An end effector, generally indicated by reference numeral 60, is pivotally mounted on an opposed end of the wrist member 52. The end effector 60 shown, is in the form of, e.g., a clip applier for anchoring clips during a surgical procedure, or the like. Accordingly, the end effector 60 has two parts or fingers 60.1, 60.2 selectively displaceable toward and away from each other in a jaw-like fashion.

It will be appreciated that the end effector 60 can be in the form of any desired surgical tool having two members, or fingers, which pivot relative to each other, such as, for example, scissors, pliers or graspers for use as needle drivers, forceps, or the like.

The end effector 60 is pivotally mounted in a clevis, generally indicated by reference numeral 62, on an opposed end of the wrist member 52, by means of an end effector pivot 64. It will be appreciated that free ends 60.3, 60.4 of the fingers 60.1, 60.2 are preferably independently selectively displaceable angularly about an end effector pivot axis 64.1, defined by the end effector pivot 64, toward and away from each other as indicated by arrows B, C. It will further be appreciated that the members 60.1, 60.2 can preferably be displaced angularly about the end effector pivot 64 to change the orientation of the end effector 60 as whole, relative to the wrist member 52. Thus, each part 60.1, 60.2 is angularly displaceable about the end effector pivot 64 independently of the other, so that the end effector 60 as a whole, is angularly displaceable about the end effector pivot 64 as indicated by arrows D. Furthermore, and as can best be seen with reference to FIGS. 2 and 3 of the drawings, the shaft 28.1 is rotatably mounted on the housing 34 for rotation about an axis 28.2 extending longitudinally along the shaft 28.1 as indicated by the arrows E. Thus, when mounted on one of the arm assemblies or arms 26, the end effector 60 has three degrees of freedom of movement relative to the arm 26, in addition to actuation movement of the end effector, namely, rotation about the axis 28.2 as indicated by arrows E, angular displacement as a whole about the pivot 64 as indicated by arrows D and angular displacement about the pivot 56 as indicated by arrows A. By moving the end effector 60 within its three degrees of freedom of movement, its orientation relative to the end 31 of the shaft 28.1 can selectively be varied. It will be appreciated that movement of the end effector 60 relative to the end 31 of the shaft 28.1, in use, is controlled by appropriately positioned actuators, e.g., electric motors, or the like, which respond to inputs from an associated master control at the control station 12, so as to drive the end effector 60 to a required orientation as dictated by movement of the associated master control.

Referring again to FIG. 4 of the drawings, each finger 60.1, 60.2 has an integrally formed pulley portion 60.5, 60.6. Each pulley portion 60.5, 60.6 defines a circumferentially extending channel 60.7, 60.7 in which an elongate actuation element in the form of, e.g., an actuation cable, is carried, as described in greater detail herein below.

Figure 3:
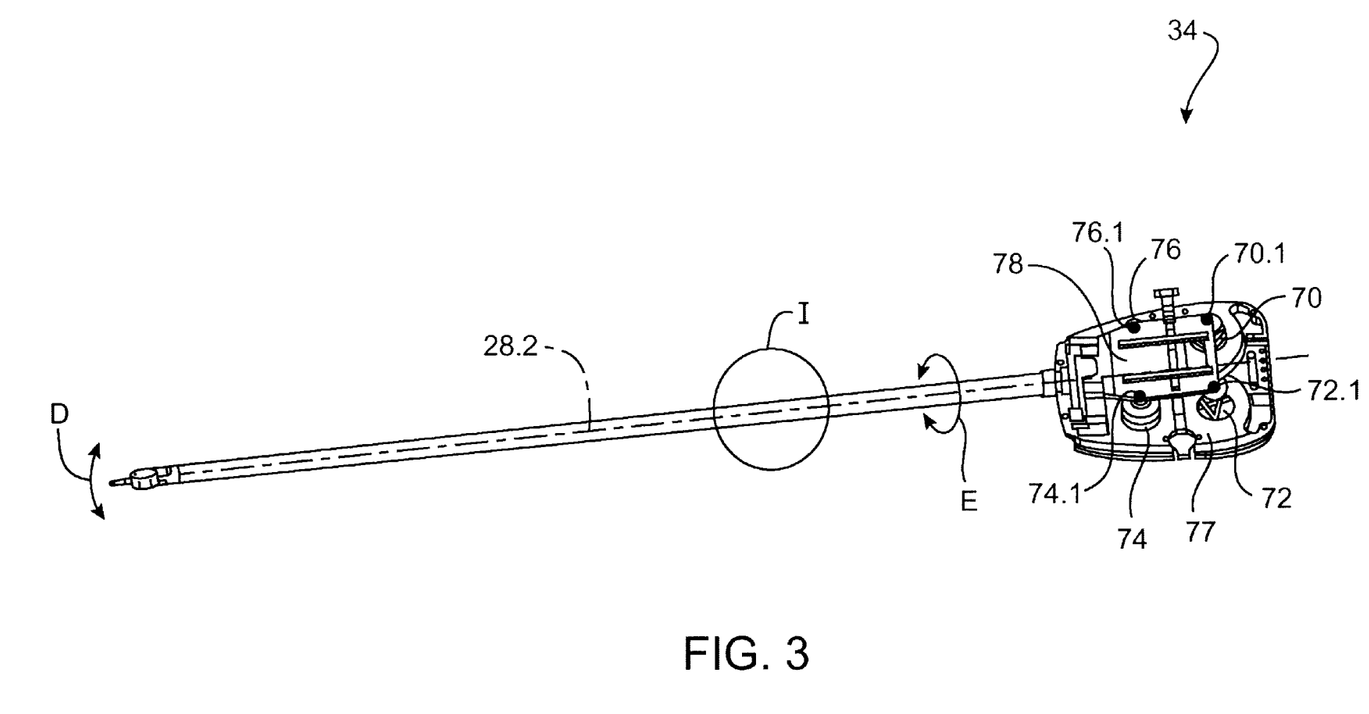
FIG. 3 shows a three-dimensional view of the surgical instrument shown in FIG. 2, a cover of a housing of the surgical instrument having been removed.

As can best be seen in FIG. 3 of the drawings, the surgical instrument 28 typically has four transmission members 70, 72, 74, and 76. The transmission members 70, 72, 74, 76 are typically in the form of drums or spools. The spools 70, 72, 74, 76 are secured on shafts 70.1, 72.1, 74.1, and 76.1, respectively. The shafts 70.1, 72.1, 74.1, 76.1 extend through a base 77 of the housing 34. Ends of the shafts 70.1, 72.1, 74.1, 76.1 are rotatably held by and between a mounting plate 78 and the base 77. Opposed ends of the shafts 70.1, 72.1, 74.1, 76.1 extend through the base 77, to an opposed side of the base, hidden from view in FIG. 3. At the opposed side, each shaft 70.1, 72.1, 74.1, 76.1 carries an engaging member (not shown) on its opposed end. Each engaging member is arranged releasably to couple with a complementary engaging member (not shown) rotatably mounted on the carriage 37 of FIG. 1. The engaging members on the carriage 37 are operatively connected to actuators (not shown), e.g., electric motors, or the like, to cause selective angular displacement of each engaging member on the carriage 37 in response to actuation of its associated actuator. Thus, selective actuation of the actuators is transmitted through the engaging members on the carriage 37, to the engaging members on the opposed ends of the shafts 70.1, 72.1, 74.1, 76.1 to cause selective angular displacement of the spools 70, 72, 74, 76. Selective angular displacement of the spools 70, 72, 74, 76 causes selective actuation of the elongate actuation elements, which in turn causes selective angular displacement of the wrist member about the wrist pivot axis 56.1, of the fingers 60.1, 60.2 about the end effector pivot axis 64.1, and of the shaft 28.1 about the axis 28.2.

It will be appreciated that the elongate actuation elements typically extend operatively between the transmission members or spools 70, 72, 74, 76 and the pulley portions 60.7, 60.7, the wrist member 52, and the shaft 28.1, respectively, so as to cause angular displacement of the spools to be transmitted to respectively the fingers 60.1, 60.2, the wrist member 52 and the shaft 28.1, thereby to cause responsive angular displacement of the fingers 60.1, 60.2 about the end effector pivot axis 64.1, the wrist member 52 about the wrist pivot axis 56.1, and the shaft 28.1 about the axis 28.2.

The surgical instrument 28 may have a shaft length, indicated at M in FIG. 2 of the drawings, of between about 250 mm and about 560 mm. The shaft preferably has a length M of about 400 mm. Furthermore, the shaft 28 preferably has an extreme outer cross-sectional dimension C, as can best be seen in FIG. 4 of the drawings, of less than about 12 mm. The shaft 28 is typically cross-sectionally circular in shape, the extreme cross-sectional dimension C then being an outer diameter of the shaft. The outer diameter C of the shaft is typically between about 3 mm and about 12 mm. Preferably, the shaft 28 has a diameter C of about 8 mm. The instrument 28 defines a length W extending between the wrist pivot axis 56.1 and the end effector pivot axis 64.1. It further defines a length L extending between the end effector pivot axis 64.1 and the free ends 60.3, 60.4 of the fingers 60.1, 60.2. A reach R of the instrument 28 is defined between the wrist pivot axis 56.1 and the free ends 60.3, 60.4 of the fingers 60.1, 60.2.

Figure 5:
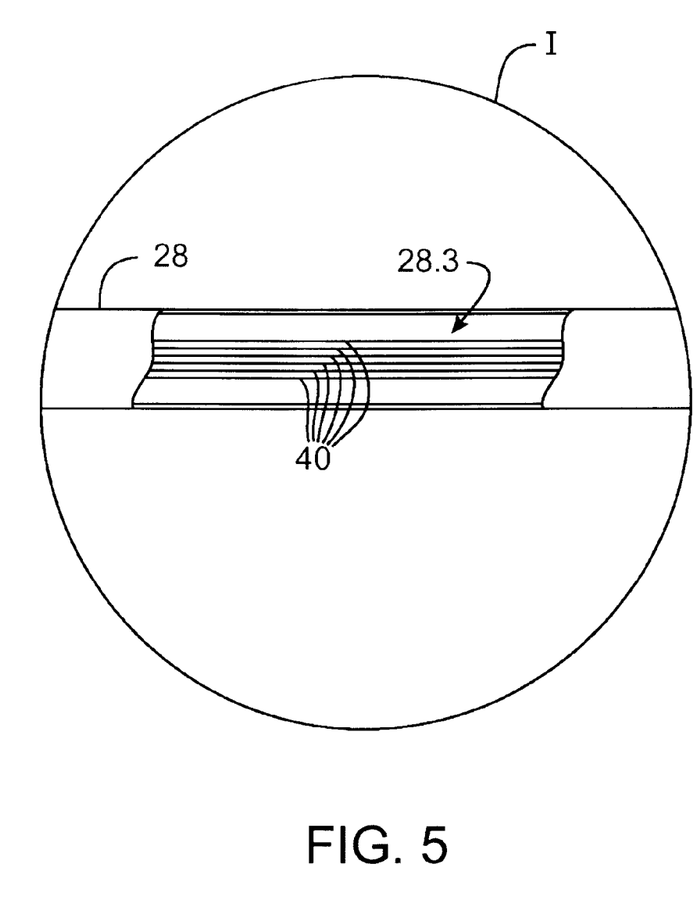
FIG. 5 shows, at an enlarged scale, a schematic sectional view of part of an elongate shaft of the surgical instrument of FIGS. 2 and 3, as indicated by the circular window I in FIG. 3.

Referring now to FIG. 5 of the drawings, the shaft 28.1 defines a longitudinally extending internal passage 28.3. The elongate actuation elements, as indicated by reference numerals 40, extend longitudinally along the shaft 28.1 within the passage 28.3.

For a further description of a surgical instrument similar to the instrument 28, refer to Applicant's co-pending patent application Ser. No. 09/398,958 filed Sep. 17, 1999 entitled "Surgical Tools for use in Minimally Invasive Surgical Applications", the full disclosure of which is incorporated herein by reference.

In minimally invasive surgery, there is a tendency to develop surgical instruments of increasingly smaller size. Depending on the specific type of surgical procedure to be performed, or the specific surgical task a surgical instrument having a specific type of end effector is to perform during a surgical procedure, using such a smaller surgical instrument can be advantagous. For instance, should the surgical procedure to be performed be at a relatively small or sensitive surgical site, or should the surgical site be relatively difficult to access, it can be advantageous to use such smaller instruments. Smaller instruments, or end effectors, enable smaller tissue portions, vessels, and the like, to be handled with greater accuracy and dexterity. Using such smaller instruments can have other advantages. For instance, using such smaller instruments can increase the number of instruments that practicably can be positioned in close proximity to a surgical site. During certain surgical procedures, a surgeon performing the surgical procedure can require using end effectors of several different types so as to perform different surgical tasks during the course of the surgical procedure. By enabling several surgical instruments having end effectors of different types to be resident in close proximity to the surgical site at the same time, the surgeon can select a desired end effector without having to retract one instrument from the surgical site so as to replace that instrument with one bearing the desired end effector. In this manner certain surgical procedures can typically be performed with greater expediency.

In spite of such advantages, it has been found that certain surgical tasks can be performed with greater ease and accuracy by actually increasing the size of certain parts or portions of such surgical instruments. One such task, for example, is suturing. When such a task is to be performed, a surgical needle is often passed between the end effector of one instrument and another. Such instruments typically define end effectors in the form of needle graspers, or holders, which typically define two fingers or working elements similar to those of the instrument 28, but arranged to grip the needle between the fingers. During a suturing task, the end effectors are often brought into close proximity relative to each other so as to enable the needle to be passed between the end effectors of the instruments. It has been found that if the reach R of the end effectors is too small, the shafts of the instruments can collide or contact each other when the needle is passed between the end effectors, thereby rendering the suturing task uncomfortable and unnecessarily problematic. Furthermore, when the reach R is too small, the robotic arms 26, 26 on which the instruments are mounted, can collide with each other when the needle is passed between the end effectors. Accordingly, when a surgical task such as suturing is to be performed, the task can be performed with greater ease and accuracy by actually extending the reach R of the end effectors thereby inhibiting collision between instrument shafts and/or robotic arms and enabling the surgical task to be performed with greater ease.

It has also been found that by extending the reach R, the range of motion which the end effector can perform is increased. Therefore, when certain movements are commanded at an associated master control, the extent to which such commanded motion can be localized to only end effector and wrist member movement also increases. Accordingly, when relatively localized movements are required, the requirement for the robotic arm 26 to participate to achieve such motion decreases. This can be advantagous because, since the robotic arm typically has greater inertia than the wrist member and the end effector, end effector and wrist member movement can normally be controlled with greater precision and performed with quicker response to master control input. In consequence, by extending the reach R, the range of desired motion that can be achieved with greater precision can also increase, thus increasing the accuracy whereby surgical tasks requiring relatively small localized ranges of motion can be performed. It will be appreciated that the chances of the surgical instrument shafts connecting or colliding is also decreased by providing such extended reach to the end effectors, not only when suturing, but in general. Furthermore, the chances of the robotic arms 26, 26 on which the instruments are mounted colliding with each other, in use, also decreases in general. Thus, the increased range of end effector movement enhances the surgeon's ability to reach around and/or behind structures or tissue in the patient body during the performance of a surgical procedure, whilst decreasing large movements of the supporting robotic arm structures and whilst inhibiting collisions between the robotic arms 26, 26, and the shafts of the instruments.

Accordingly, although the surgical instrument 28, when used with the telesurgical system 10, can satisfactorily perform a variety of different surgical tasks, certain tasks can actually be performed with greater expediency by increasing the reach R of the instrument.

In accordance with this invention, a novel surgical instrument, similar to the surgical instrument 28, is provided. The surgical instrument preferably has a reach R that is increased by increasing the length L of the end effector members relative to the distance W. Ratios of L:W of at least about 2:1 or greater are preferred. In a specific embodiment, a surgical instrument preferably has a reach R falling in the range between about 28 mm and 40 mm (about 1⅛ and 1⅗ inches), although larger reaches are possible.

In one preferred embodiment of the invention the distance W is about 10 mm (about ⅜ inch), the length L then being at least about 18 mm so as to provide a reach R of at least about 28 mm. Accordingly, in this embodiment, the length L is about twice as long as the length W.

Figure 6:
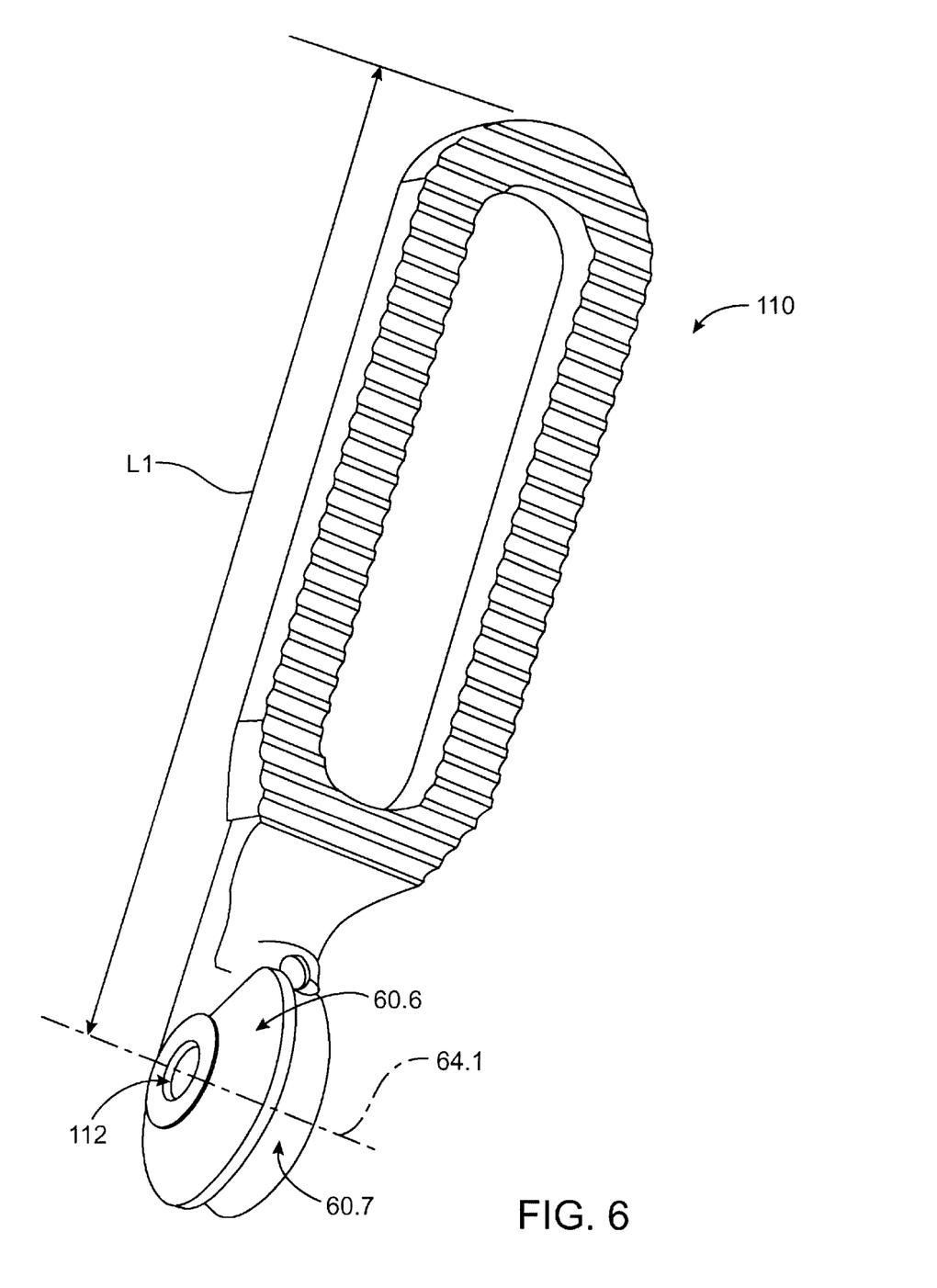
FIG. 6 shows a three-dimensional view of part of an end effector, in the form of forceps, of a surgical instrument in accordance with a preferred embodiment of the invention.

Part of such a preferred instrument, in accordance with the invention, is indicated in FIG. 6 of the drawings, in which like reference numerals are used to designate similar parts or features, unless otherwise stated. FIG. 6 shows a finger, or working element 110, of a surgical instrument defining an end effector in the form of a forceps for handling tissue so as to inhibit inadvertant damage to the tissue. The finger 110 preferably has a length L1 of at least about 18 mm (about ¾ inches). It will be appreciated that the finger 110, in use, is mounted on a wrist member of an instrument similar to the instrument 28. When in a mounted condition, the end effector pivot axis 64.1 extends centrally through a hole 112 through which the end effector pivot 64 also extends. Another advantage in providing such a forceps, is that relatively large tissue portions, relatively large vessels, and the like, can be handled with greater ease.

Figure 7:
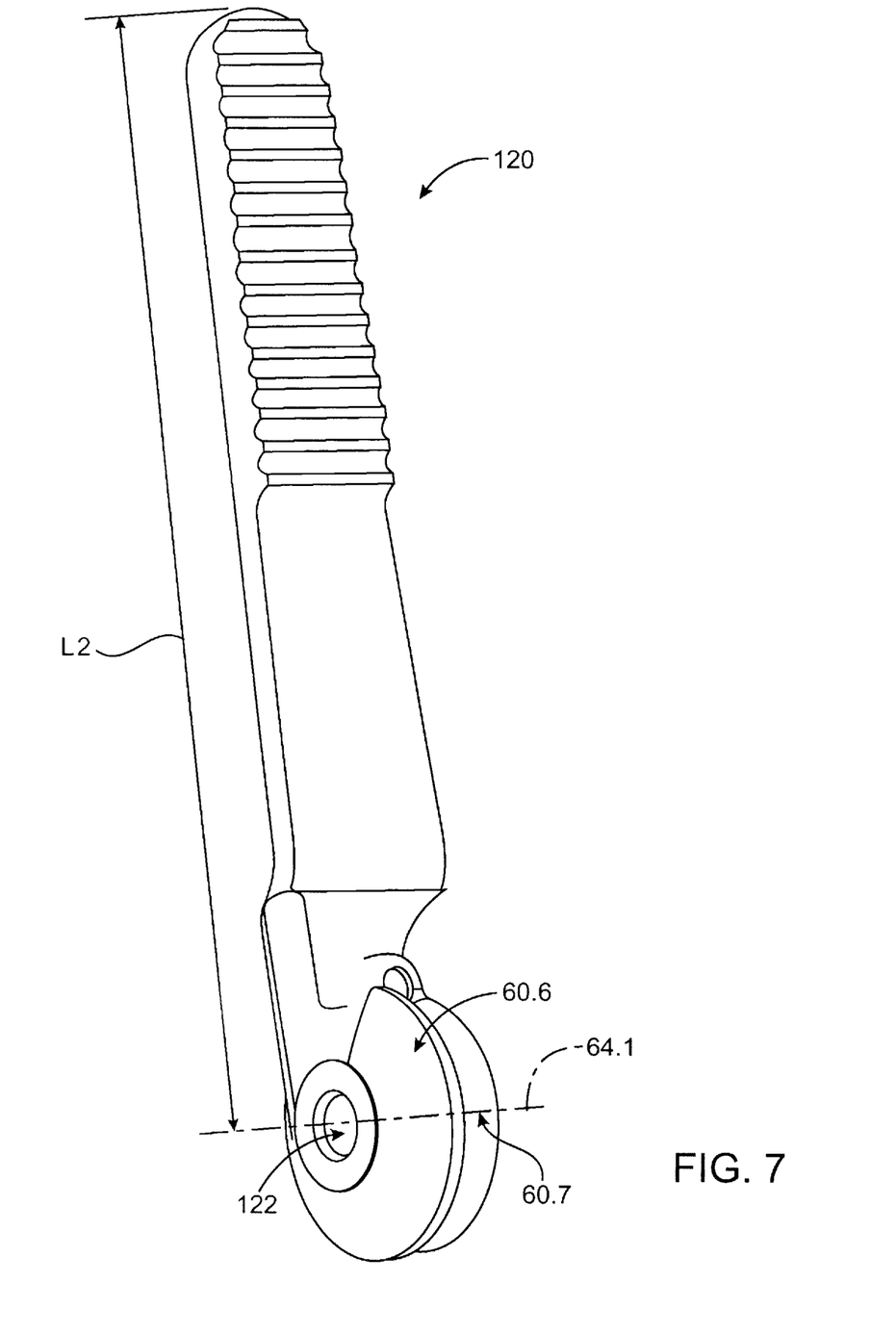
FIG. 7 shows a three-dimensional view of part of an end effector, in the form of graspers, of another surgical instrument in accordance with a preferred embodiment of the invention.

Part of another instrument, in accordance with a preferred embodiment of the invention, is indicated in FIG. 7 of the drawings, in which like reference numerals are used to designate similar parts or features, unless otherwise stated. FIG. 7 shows a finger, or working element 120, of a surgical instrument defining an end effector in the form of a gripper, or grasper, typically used to grasp objects, such as needles, and the like. The finger 120 has a length L2 of at least about 18 mm (about ¾ inches). It will be appreciated that the finger 120 is also, in use, mounted on a wrist member of an instrument similar to the instrument 28. When in a mounted condition, the end effector pivot axis 64.1 extends centrally through a hole 122, through which the end effector pivot 64 also extends.

The distances L1, L2 of the improved surgical instruments of the preferred dimensions herein described typically fall in the range between about 18 mm to about 30 mm, although larger lengths are possible. Preferably, the length falls in the range between about 18 mm and about 22 mm.

Figure 8:
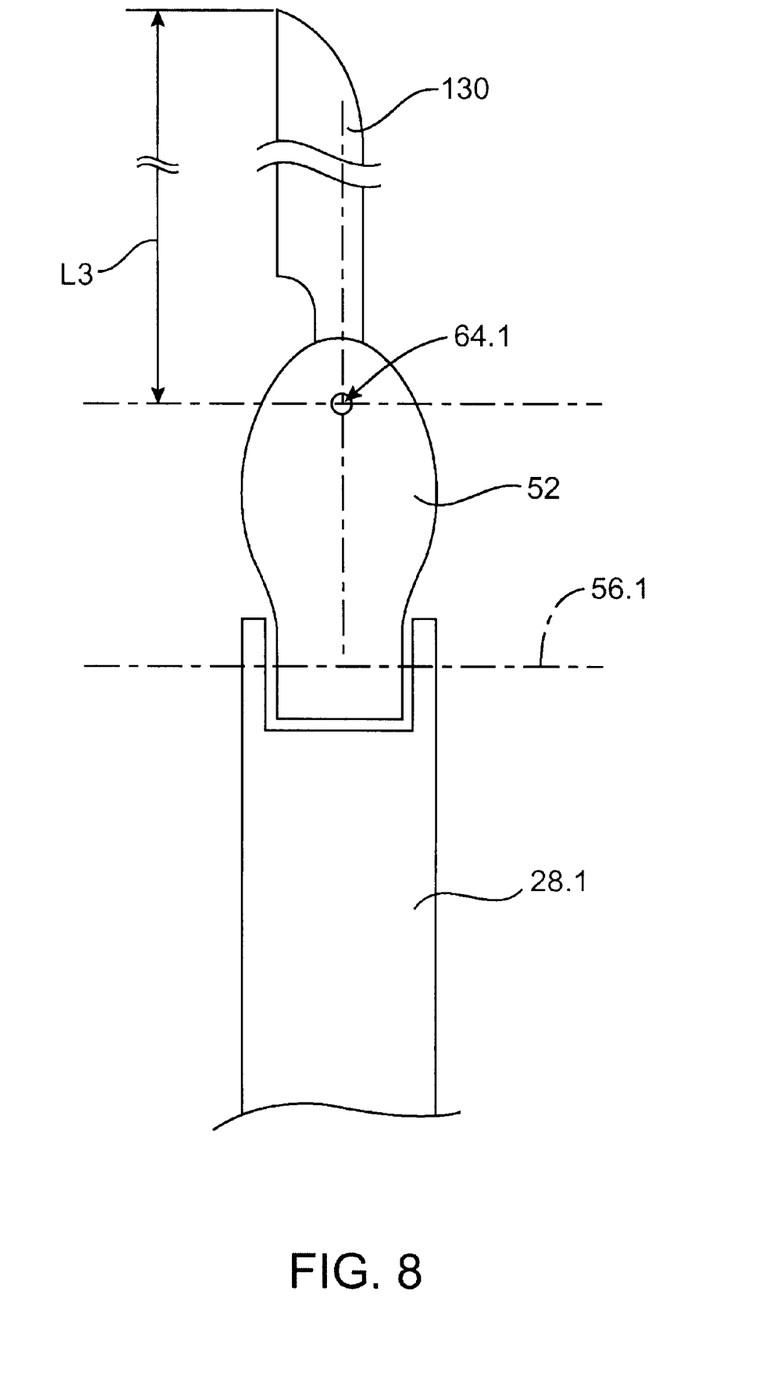
FIG. 8 shows a schematic side view of another surgical instrument in accordance with the invention, the surgical instrument having a single working member in the form of a scalpel.

Although, by way of example, the invention has been described with reference to end effectors comprising two working elements, or fingers, angularly displacable relative to each other, the invention is not to be interpreted as being limited to such instruments only. Accordingly, the invention extends to surgical instruments having end effectors typically comprising only a single working element, or finger. Such single working member end effectors include blades or scalpels, electrocautery blades or electrodes, and the like. Accordingly, the invention extends to surgical end effectors having a single working element wherein the reach R of the instrument is increased by increasing the ratio of L:W to at least about 2:1. In a preferred embodiment, R is at least about 28 mm. This can be achieved by providing a single working element defining a length extending between a free end thereof and the end effector pivot axis 64.1, on the wrist member 52, of at least about 18 mm. FIG. 8, in which like reference numerals are used to designate similar parts or features, unless otherwise stated, shows an example of an instrument defining an end effector having a single working element, or member, in the form of a scalpel 130, in accordance with the invention, in which the length L3 is at least about 18 mm with a L:W ratio of at least about 2:1.

Figure 9:
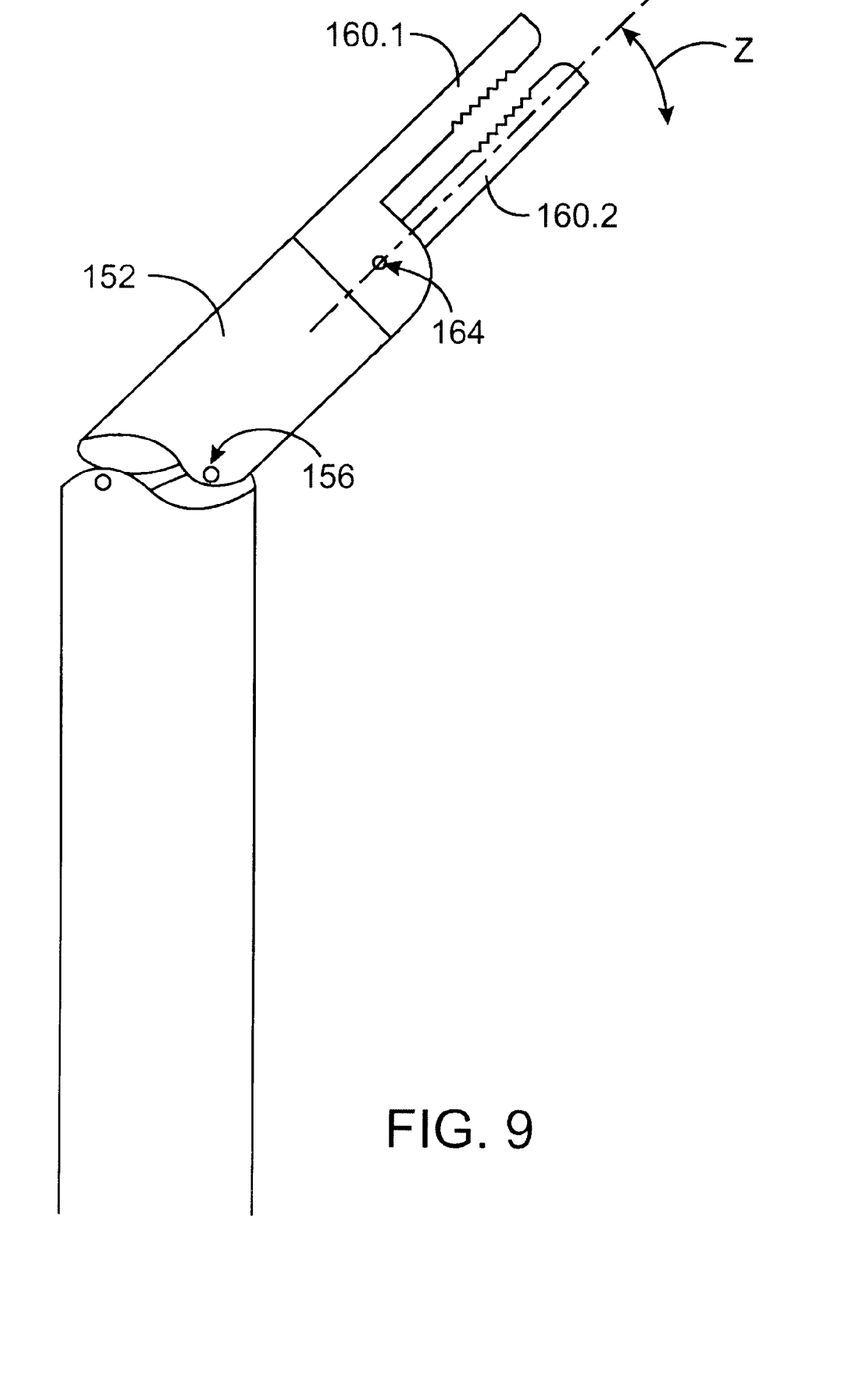
FIG. 9 shows a schematic side view of another surgical instrument in accordance with the invention.

Furthermore, it is to be appreciated that where reference is made to the end effector having two working members, or fingers, which are angularly displacable relative to each other, both fingers need not necessarily be angularly displacable relative to the wrist member, to be angularly displacable relative to each other. For example, and as can best be seen with reference to FIG. 9 of the drawings, the one finger 160.1 can be fixed relative to the wrist member 152, only the other finger 160.2 being pivotally connected to the wrist member 152 at 164, to enable the fingers 160.1, 160.2 to be angularly displacable relative to each other, as indicated by arrows Z. Furthermore, the wrist axis can be defined by a universal type coupling 156 as indicated in FIG. 9 and need not be in the form of a fixed pivotal connection as indicated in FIG. 4 of the drawings.

Another method of increasing the reach R of the end effector is to increase the distance W relative to distance L, as can best be seen with reference to FIG. 4 of the drawings, between the wrist pivot axis 56.1 and the end effector pivot axis 64.1. Accordingly, the distance W can be increased to achieve a ratio of W:L of at least about 2:1. In a preferred embodiment, W is increased to at least about 18 mm (about ¾ inch) while the length L is selected to be at least about 10 mm (about ⅜ inch), thereby to extend the reach R to at least about 28 mm (about 1⅛ inch). In such a case, the distance W is about twice the distance L.

Figure 10:
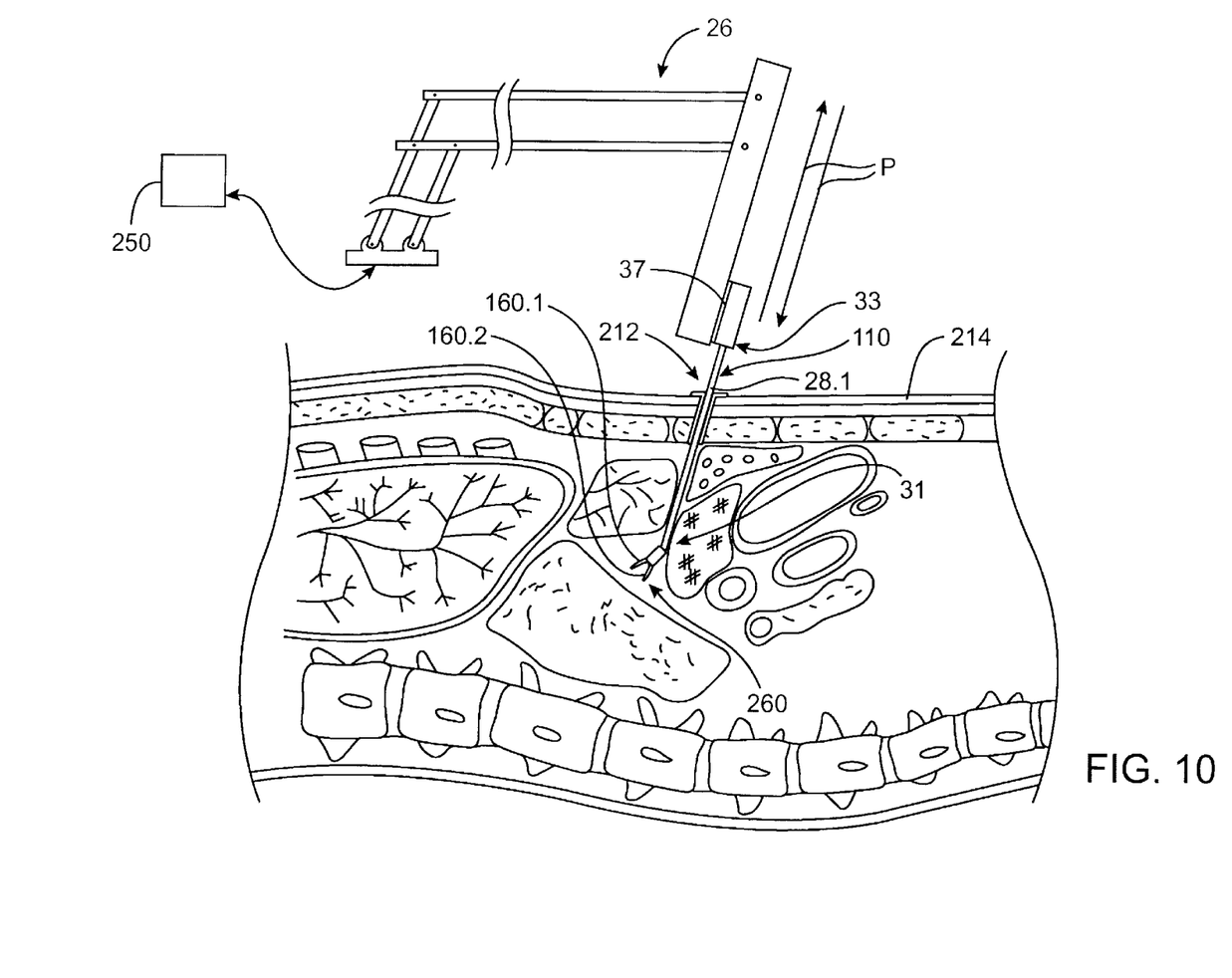
FIG. 10 shows a schematic side view of one of the surgical instruments in accordance with the invention shown in FIGS. 6 and 7 with reference to FIG. 4, in use.

With reference to FIG. 10 of the drawings, in use, the surgical instrument in accordance with the invention, is passed through an entry port 212 in a patient body 214 such that the end effector indicated at 260 is positioned within the patient body and the opposed end 33 of the shaft 28.1 is positioned outside the patient body. The instrument is typically connected in a robotically controlled system, part of which is indicated schematically at 250. It will be appreciated that to connect the surgical instrument in the robotically controlled system 250, it is typically mounted on the carriage 37 on one of the arms 26, as indicated in FIG. 1, and as schematically indicated in FIG. 10. In this manner, the end effector 260 can be actuated from outside the patient body 214 by means of the robotically controlled system 250 so as to cause the fingers selectively to move toward and away from each other so as to perform at least part of the surgical procedure.

The end effector 260 is typically actuated by means of the robotically controlled system by causing the system to actuate the elongate actuation elements 40 (not shown in FIG. 10) extending internally along the shaft 28.1. As already mentioned, the actuation elements are operatively connected to the end effector at the one end 31 of the shaft 28.1 so as to enable the fingers of the end effector selectively to be displaced angularly about the end effector pivot axis 64.1 by selective actuation of the elongate actuation elements. The robotically controlled system 250 typically causes the elongate actuation element to be actuated in response to master control input. To connect the surgical instrument in the robotically controlled system, the instrument is typically releasably mounted on the carriage 37 of one of the robotically controlled arms 26.

While exemplary embodiments have been described in some detail, for clarity of understanding and by way of example, a variety of modifications, changes, and adaptations will be obvious to those with skill in the art. For instance, the end effectors need not be actuatable by means of flexible elements in the form of cables, but, instead, or in addition, can be actuatable by longitudinally extending shafts, or rods, extending within the shaft 28.1 of the instrument, for example. In such a case, the pulley portions on the end effectors may not be required. Therefore, the scope of the present invention is limited solely by the appended claims.

What is claimed is:

1. A surgical instrument comprising
   an elongate shaft defining opposed ends;
   an end effector mounted at one of the ends of the shaft, the end effector having two fingers pivotally connected relative to each other to be angularly displaceable relative to each other about an end effector pivot axis at the one end of the shaft, each finger defining a free end remote from the end effector pivot axis and being of a length defined between its free end and the end effector pivot axis of at least 18 mm; and
   a robotic control system coupled to the shaft for effecting movements and actuation of the end effector.

2. A surgical instrument as claimed in claim 1, which further comprises a wrist member defining an end effector pivot and a wrist pivot spaced from the end effector pivot, the fingers of the end effector being pivotally connected to each other on the end effector pivot and the wrist member being pivotally mounted on the end of the shaft by means of the wrist pivot to be angularly displaceable relative to the shaft about a wrist pivot axis defined by the wrist pivot.

3. A surgical instrument as claimed in claim 2, wherein the end effector pivot axis and the wrist pivot axis extend at an angle relative to each other.

4. A surgical instrument as claimed in claim 3, wherein the end effector pivot axis and the wrist pivot axis extend generally perpendicularly relative to each other.

5. A surgical instrument as claimed in claim 2, which further comprises at least one elongate actuation element extending along the shaft, the elongate actuation element being operatively connected to the wrist member at the one end of the shaft so as to enable the wrist member selectively to be displaced angularly about the wrist pivot axis by selective actuation of the elongate actuation element.

6. A surgical instrument as claimed in claim 5, which further comprises at least one transmission member mounted on the other end of the shaft, the transmission member being operatively associated with the elongate actuation element so as to cause actuation of the elongate actuation element in response to actuation of the transmission member.

7. A surgical instrument as claimed in claim 1, which further comprises at least one elongate actuation element extending along the shaft, the actuation element being operatively connected to the end effector at the one end of the shaft so as to enable the fingers of the end effector selectively to be displaced angularly relative to each other about the end effector pivot axis by selective actuation of the elongate actuation element.

8. A surgical instrument as claimed in claim 7, which further comprises at least one transmission member mounted on the other end of the shaft, the transmission member being operatively connected to the elongate actuation element so as to cause actuation of the elongate actuation element in response to actuation of the transmission member.

9. A surgical instrument as claimed in claim 7, which comprises at least two elongate actuation elements extending along the shaft, one of the actuation elements being operatively connected to one of the fingers of the end effector and the other elongate actuation element being operatively connected to the other finger of the end effector, each finger selectively being displaceable angularly about the end effector pivot axis independently of the other by selective actuation of the elongate actuation elements.

10. A surgical instrument as claimed in claim 9, which further comprises at least two transmission members mounted on the other end of the shaft, the transmission members being operatively connected to the elongate actuation elements so as to cause selective actuation of the elongate actuation elements in response to selective actuation of the transmission members.

11. A surgical instrument as claimed in any one of claims 7 to 6 inclusive, wherein the elongate shaft defines an internal longitudinally extending passage, the or each elongate actuation element being positioned inside the passage to extend internally along the shaft.

12. A surgical instrument as claimed in any one of claims 7 to 6 inclusive, in which the or each elongate actuation element is at least partially defined by a length of cable.

13. A surgical instrument as claimed in claim 12, wherein the or each transmission member is in the form of a spool arranged selectively to be driven to displace angularly thereby to actuate the or each elongate actuation element.

14. A surgical instrument as claimed in claim 7, wherein at least one of the fingers of the end effector defines a pulley portion through which the end effector pivot axis extends, the at least one elongate actuation element extending around the pulley portion.

15. A surgical instrument as claimed in claim 1, wherein the length falls in the range between about 18 mm and 30 mm.

16. A surgical instrument as claimed in claim 15, wherein the length falls in the range between about 18 mm and 22 mm.

17. A surgical instrument as claimed in claim 1, wherein the shaft has a length of between about 380 mm and about 560 mm.

18. A surgical instrument as claimed in claim 17, wherein the shaft has a length of about 400 mm.

19. A surgical instrument as claimed in claim 1, wherein the shaft has an extreme outer cross sectional dimension of less than about 12 mm.

20. A surgical instrument as claimed in claim 19, in which the shaft is cross sectionally circular, the extreme outer cross sectional dimension then being an outer diameter of the shaft, the outer diameter of the shaft being between about 5 mm and about 12 mm.

21. A surgical instrument as claimed in claim 20, in which the shaft has an outer diameter of about 8 mm.

22. A method of performing a surgical procedure, the method comprising passing a surgical instrument having an elongate shaft, at one end of which an end effector is mounted, through an entry port in a patient body into a position in which the end effector is positioned within the patient body and an opposed end of the shaft is positioned outside the patient body, the end effector having at least one working member pivotally connected at the one end of the shaft to be angularly displaceable about an end effector pivot axis, the working member defining a free end remote from the end effector pivot axis and being of a length defined between its free end and the end effector pivot axis of at least 18 mm;

connecting the surgical instrument in a robotically controlled system; and actuating the end effector from outside the patient body by means of the robotically controlled system so as to cause the working member selectively to displace angularly about the end effector pivot axis thereby to perform at least part of the surgical procedure.

23. A method of performing a surgical procedure as claimed in claim 22, in which the surgical instrument comprises at least one elongate actuation element extending along the shaft, the actuation element being operatively connected to the end effector at the one end of the shaft so as to enable the working member to be selectively displaced angularly about the end effector pivot axis by selective actuation of the elongate actuation element at the opposed end of the shaft, actuating the end effector from outside the patient body by means of the robotically controlled system then including causing the robotically controlled system to actuate the elongate actuation element.

24. A method of performing a surgical procedure as claimed in claim 23, wherein connecting the surgical instrument in a robotically controlled system includes releasably mounting the surgical instrument on a robotically controlled arm.

25. A surgical instrument comprising an elongate shaft defining opposed ends; and an end effector mounted at one of the ends of the shaft, the end effector defining a working member pivotally connected at the one end of the shaft to be angularly displaceable relative to the shaft about an end effector pivot axis at the one end of the shaft, the working member defining a free end remote from the end effector pivot axis and being of a length defined between its free end and the end effector pivot axis of at least 18 mm.

26. A surgical instrument as claimed in claim 25, wherein the length falls in the range between about 18 mm and 30 mm.

27. A surgical instrument as claimed in claim 26, wherein the length falls in the range between about 18 mm and 22 mm.

28. A surgical instrument comprising an elongate shaft defining opposed ends;

a wrist member pivotally connected at one end of the shaft to be angularly displaceable relative to the shaft about a wrist pivot axis at the one end of the shaft; and an end effector defining at least one working member, the working member being pivotally connected on the wrist member about an end effector pivot axis, spaced from the wrist pivot axis, to be angularly displaceable relative to the wrist member, the working member defining a free end remote from the end effector pivot axis, the distance between the free end of the working member and the end effector pivot axis being at least about twice as large as the distance between the end effector pivot axis and the wrist pivot axis.

\* \* \* \* \*